(12) United States Patent
Wild

(10) Patent No.: US 7,066,964 B2
(45) Date of Patent: Jun. 27, 2006

(54) PROSTHETIC KNEE AND ROTARY HYDRAULIC CHAMBER

(75) Inventor: Grant E. Wild, Horton, MI (US)

(73) Assignee: Hosmer-Dorrance Corporation, Campbell, CA (US)

( * ) Notice: Subject to any disclaimer, the term of this patent is extended or adjusted under 35 U.S.C. 154(b) by 0 days.

(21) Appl. No.: 10/799,220

(22) Filed: Mar. 12, 2004

(65) Prior Publication Data

US 2005/0203639 A1    Sep. 15, 2005

(51) Int. Cl.
A61F 2/64 (2006.01)
A61F 2/68 (2006.01)

(52) U.S. Cl. .......................... 623/42; 623/46
(58) Field of Classification Search ............. 623/42–46
See application file for complete search history.

(56) References Cited

U.S. PATENT DOCUMENTS

| | | | | |
|---|---|---|---|---|
| 2,282,952 A | * | 5/1942 | Erickson | 623/30 |
| 5,314,498 A | | 5/1994 | Gramnas | |
| 5,704,945 A | | 1/1998 | Wagner | |
| 5,728,173 A | * | 3/1998 | Chen | 623/44 |
| 5,800,566 A | | 9/1998 | Gramnas | |
| 5,888,212 A | | 3/1999 | Petrofsky | |
| 6,106,560 A | | 8/2000 | Boender | |
| 6,113,642 A | | 9/2000 | Petrofsky | |
| 6,423,098 B1 | | 7/2002 | Biedermann | |

OTHER PUBLICATIONS

Otto Bock-Habermann Modular Knee Joint, Polycentric, Four Bar Linkage Product Manual.
Otto Bock Modular Knee Joint with Rotary Hydraulic—Model 3R80—Product Manual.
Otto Bock Modular Knee Joint with Rotary Hydraulic—Model 3R80=1—Product Manual.
Otto Bock Modular Single Axis Knee Joint with Stance Control and Constant Friction Product Manual.
Otto Bock Modular Single Axis Knee Joints with Internal Extension Assist and Constant Friction Product Manual.
OSSUR Total Knee 2100 Geometric Locking System Product Manual.
OSSUR Total Knee 2000 Geometric Locking System Product Manual.
OSSUR Academy Alignment Recommendation Total Knee Presentation.

* cited by examiner

Primary Examiner—Bruce Snow
(74) Attorney, Agent, or Firm—Miller & Martin PLLC

(57) ABSTRACT

An improved prosthetic knee joint utilizes a rotary hydraulic chamber with internal flow control and positioned with hydraulic chamber opposite the upper joint section. A polycentric knee joint is provided with a forward flexion bumper and a cable extension assist for improved gait performance.

11 Claims, 6 Drawing Sheets

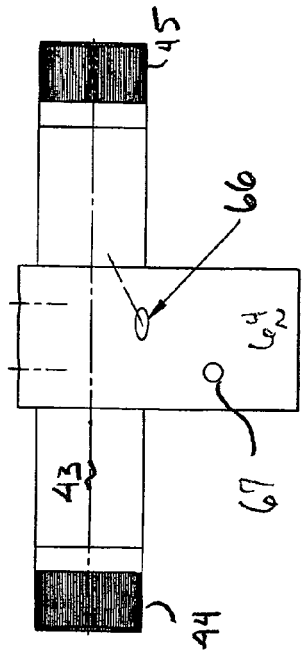
FIG. 2A
FIG. 2B
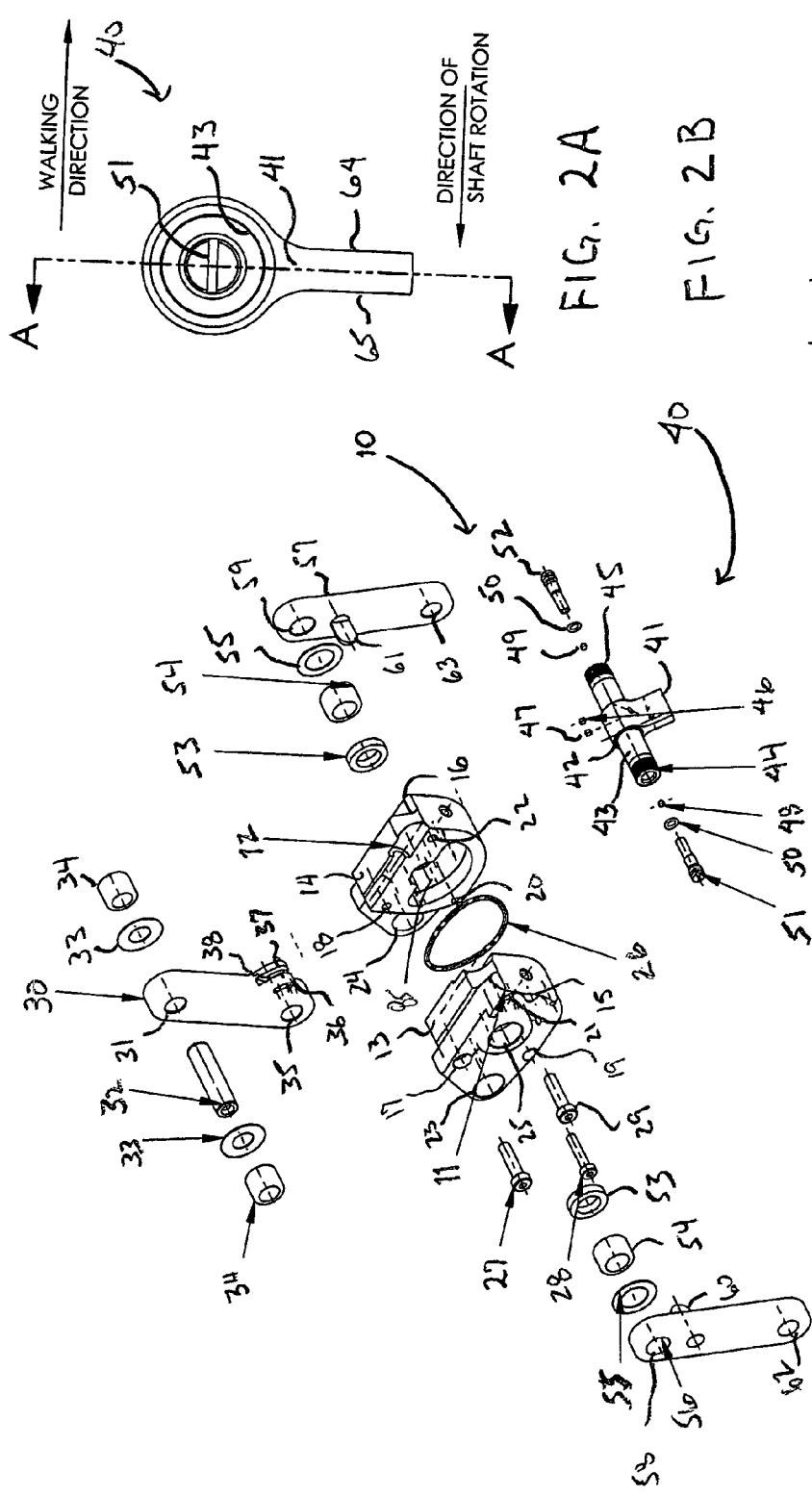
FIG. 1

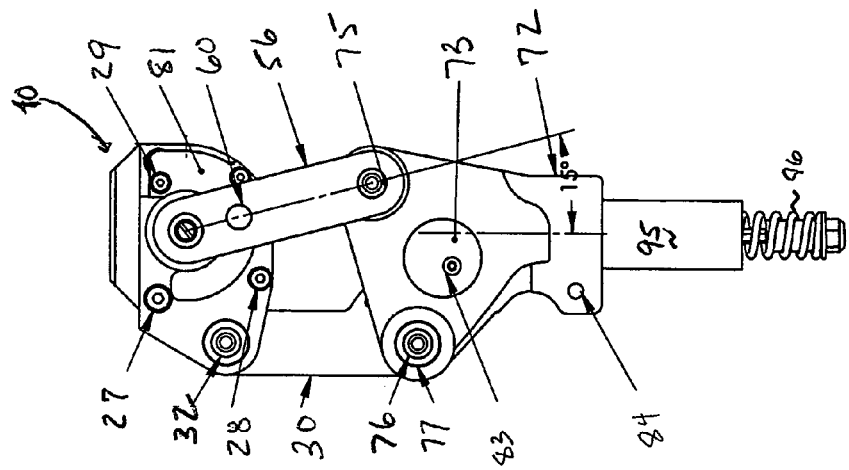
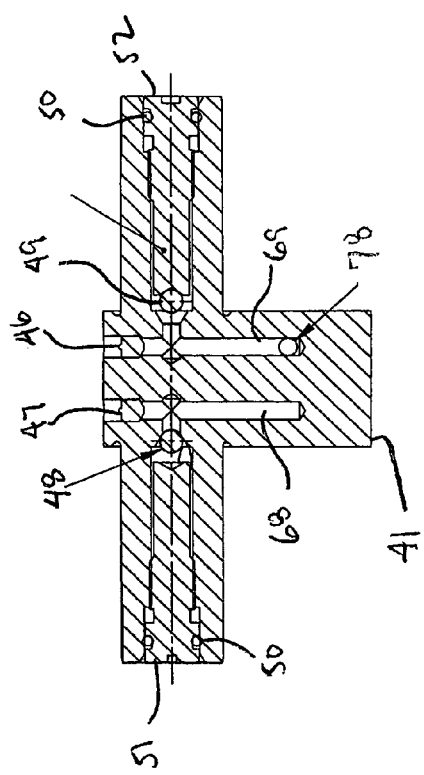
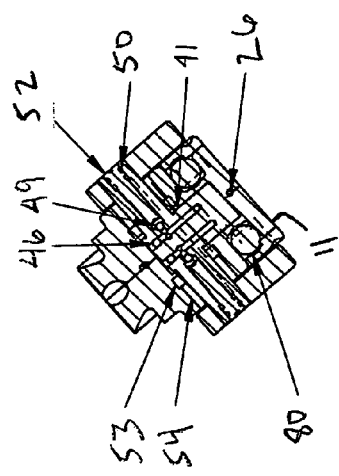

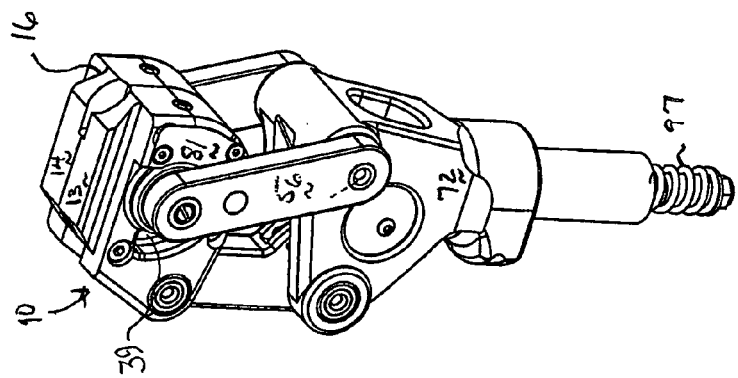
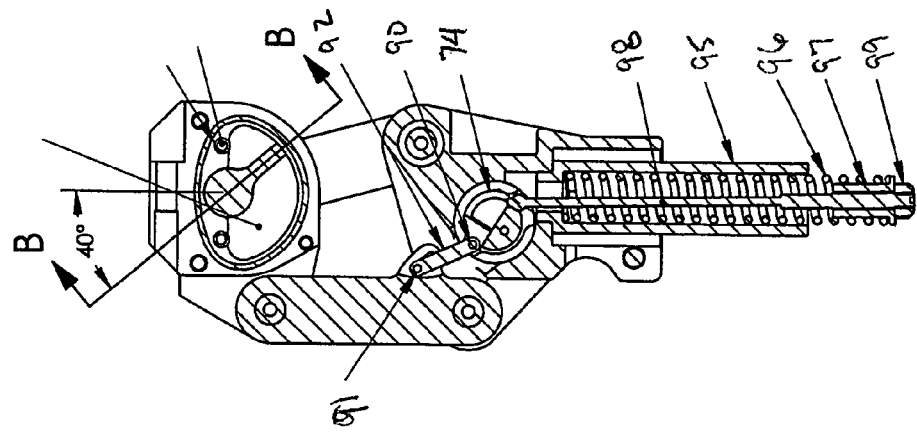
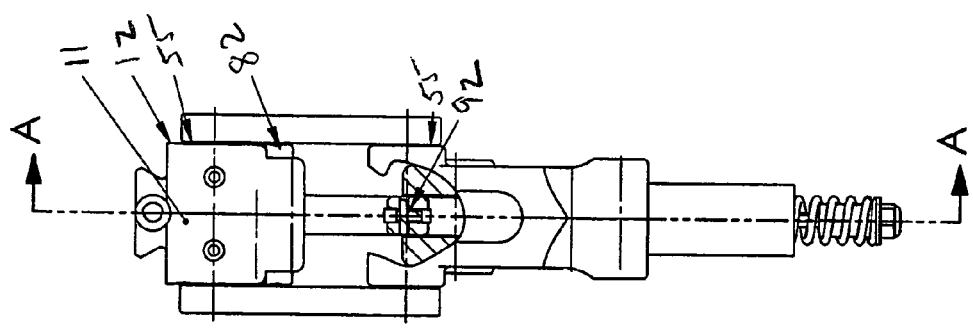

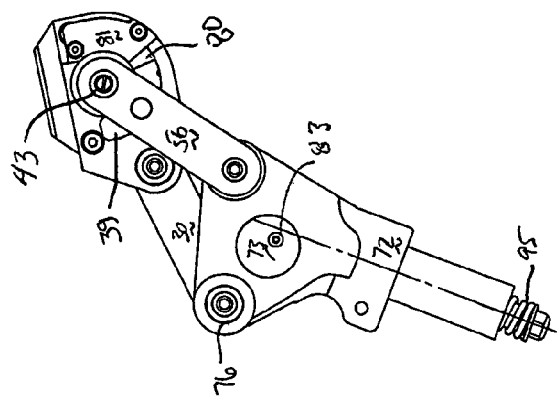
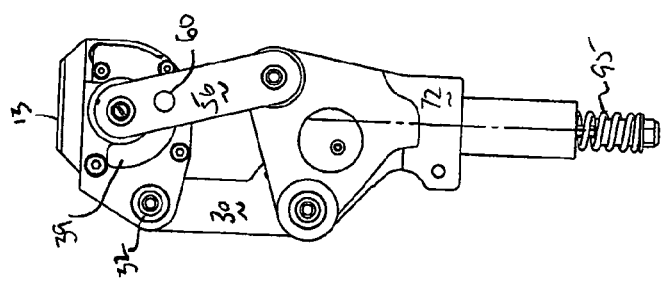
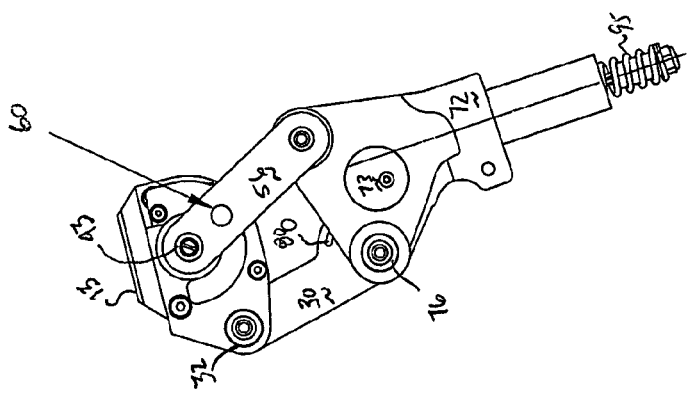
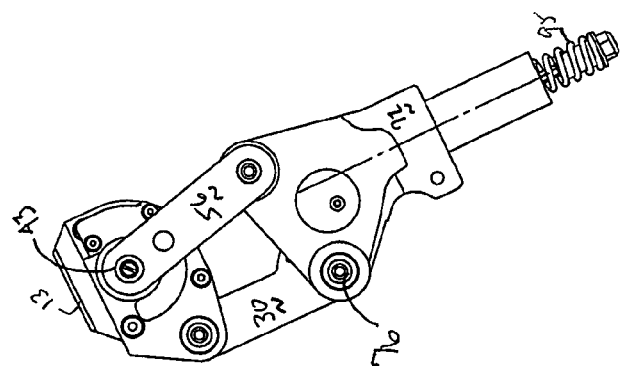

PROSTHETIC KNEE AND ROTARY HYDRAULIC CHAMBER

FIELD OF THE INVENTION

The present invention relates to prosthetic knees, in particularly to improved prosthetic knee designs that may advantageously utilize a rotary hydraulic chamber for damping and to adjust the ease of flexion and extension of the knee.

BACKGROUND OF THE INVENTION

Prosthetic knees are generally designed to allow above-the-knee amputees to replicate the biomechanical movements of a human knee joint and to permit an appropriate level of activity and stability to the wearer. In biomechanical terms, the human body is generally divided by sagittal and coronal planes. The sagittal plane is a vertical plane running from front to back, dividing the body into left and right sides. The coronal plane, or frontal plane, is a vertical plane running from side to side at right angles to the sagittal plane and therefore divides the body into front and back. Prosthetic knees offer no special function in the coronal plane and, thus, the discussion of relevant gait biomechanics occurs in the sagittal plane.

The gait cycle includes both stance and swing phases, each of which may be further subdivided into initial, intermediate and final phases. The stance phase begins with initial contact of the forward limb or "heel strike," with the hip flexed and knee extended. Loading begins to occur as the body carries forward and includes elements of shock absorption, weight bearing stability, and preservation of forward motion. The body progresses forward to mid-stance and then over the ankle and the limb lags behind the body with the heal rising and preferably the knee flexing slightly in preparation for swing phase. In swing phase, increasing the hip and knee flexion advances the limb and in mid-swing the knee will move into extension. In biomechanical terms, flexion usually indicates decrease in the angle between body segments, or in this case bending at the hip and knee, while extension indicates an increase in the angle. The swing phase ends when the limb again touches the floor.

Historically, prosthetic knees evolved with the creation of constant friction or single axis prosthesis consisting of a simple axle connecting shank segments. Modern versions will usually have an adjustable friction cell and spring loaded extension assist to improve swing phase function.

Subsequently, stance control prostheses were developed utilizing weight-activated braking mechanisms to add resistance to bending or flexion during stance only. A brake might consist of a spring-loaded brake bushing that binds when loaded during stance phase but is released during swing phase.

More complex polycentric prosthetic knees then evolved, most having four pivot points and often referred to as "four bar linkage" devices, with multiple centers of rotation. The positioning of the polycentric rotations with respect to the ground reaction line and the joint line determines the stability of the device during stance and the amount of voluntary control the amputee has over the prosthesis.

Fluid control devices comprise another principal category of prosthetic knees and utilize liquid or gas-filled cylinders and pistons to provide hydraulic or pneumatic cadence control. Generally, a piston moves axially from one end of the cylinder towards the other and is aligned in the sagittal plane. Many of the more recent prosthesis designs are hybrids which combine some of the properties of two or more of the principal categories of prostheses. The most modern and costly designs will even incorporate microprocessors to control and modify the characteristics of the prosthesis during gait and changing gait conditions.

Numerous difficulties exist in designing an effective knee prosthesis. For example, the use of liquid or gas-filled chambers may affect the ability to locate the centers of polycentric rotation in a polycentric knee; and prosthetic knees may develop very high operating temperatures due to the number of repetitions involved in ambulation and the necessarily small components and confined spaces available within the prosthesis. Furthermore, it is desirable to provide a polycentric knee with some flexion action in stance phase and to provide the extension assist mechanisms to improve gait function in the final portion of the swing phase. Thus, the development of more reliable prosthetic joints that comfortably allow the wearer increased activity and stability remains an objective of prosthetic design.

SUMMARY OF THE INVENTION

It is therefore an object of the invention to provide an improved rotary hydraulic chamber apparatus useful for fluid control in a polycentric or other knee prosthesis. It is further an object of the invention to provide improved polycentric knee prostheses that allow flexing action of the knee joint in stance phase and provide extension assist in swing phase.

According to the invention, an improved hydraulic chamber apparatus is provided with valving contained in a rotatable shaft connected to a paddle in the hydraulic chamber where the paddle rotates relative to the chamber as the knee proceeds through phases of flexion and extension. The rotary hydraulic chamber apparatus is designed to dissipate heat and minimize the height of the chamber to facilitate location of the top of the prosthesis close to the joint line. When utilized in a polycentric knee, a polyurethane bumper may be employed to permit slight flexion of the knee, while being restrained by compression against the bumper. A cable operated extension assist may also be provided.

BRIEF DESCRIPTION OF THE DRAWINGS

FIG. 1 is an exploded perspective view of the components of an improved hydraulic chamber apparatus for prosthetic knee according to the present invention.

FIG. 2A is a side plan view of an improved paddle assembly according to the present invention.

FIG. 2B is a front plan view of the improved paddle assembly.

FIG. 2C is a front sectional view of the improved paddle assembly taken along line A—A at FIG. 2A.

FIG. 3A is a side plan view of an improved polycentric knee according to the invention.

FIG. 3B is a front plan view of the improved polycentric knee of FIG. 3A.

FIG. 3C is a sectional side view of the improved polycentric knee taken along line A—A of FIG. 3B.

FIG. 3D is a sectional top plan view of the improved polycentric knee taken along line B—B of FIG. 3C.

FIG. 3E is a perspective view of the improved polycentric knee of FIG. 3A.

FIG. 4A is a side plan view of a prosthetic knee according to the invention at full extension.

FIG. 5A is a side view of the polycentric knee of FIG. 4A at 15° stance flexion.

FIG. 5C is a side sectional view of a portion of the polycentric knee of FIG. 5A showing a bumper.

FIG. 6A is a side view of the polycentric knee of FIG. 4A at full extension in mid-stance.

FIG. 7A is a side view of the polycentric knee of FIG. 4A at 45° flexion.

DETAILED DESCRIPTION OF THE INVENTION

Figure 3F:
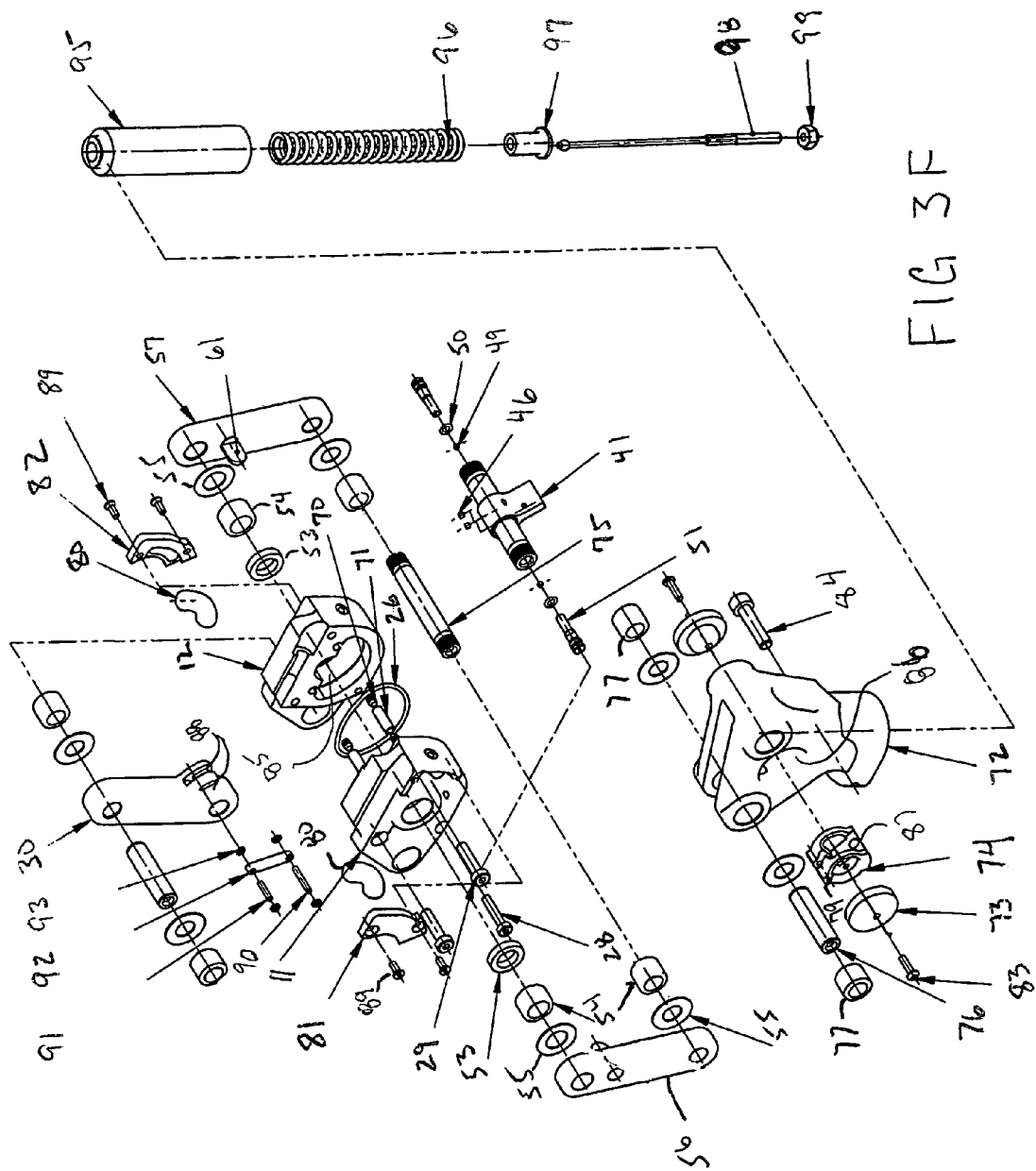
FIG. 3F is an exploded perspective view of the improved polycentric knee of FIG. 3A.

Turning first to FIG. 1, an exploded view of rotary hydraulic chamber assembly 10 which supports paddle assembly 40 is shown. Of principal importance are left and right hydraulic housings 11, 12, which when joined together and sealed with O-ring 26, define chamber 85. Rotary chamber 85 is generally in the shape of an arc of a cylinder to cooperate with rotary movement of paddle assembly 40. Paddle assembly 40 is mounted within chamber 85 which is filled with fluid, preferably silicone oil. In operation, front links 56 and 57 are mounted about left and right shaft ends 44, 45 respectively of rotatable shaft 43, and in operation rotary motion of the front links causes paddle 41 to move through fluid in chamber 85 as described below. Paddle 41 has the same general shape as the interior of chamber 85, so that the paddle 41 interfits closely with the chamber. Left and right hydraulic housings 11, 12 are shown with first apertures 17, 18, second apertures 19, 20, and third apertures 21, 22, each of which receive locking means such as screws 27, 28 and 29 to securely form the chamber 85. The upper portion of housings 11, 12 form the upper joining section and as illustrated comprise top surfaces 13, 14 respectively, which define below them grooves 15, 16, and when joined together form the base of a dovetail joint to which an upper residual limb socket may be secured. The upper leg prosthesis may be a residual limb socket, a residual limb socket with adaptor, an attachment to the wearer's skeletal structure or other prosthesis. Housings 11, 12 also have central opening 25 in which the shaft ends 44, 45 are received. Mounted on the shaft ends are radial seals 53 and needle bearings 54 to permit rotation of the shaft 43 with respect to the housings 11, 12. Upper apertures 58, 59 of front links 56, 57 are then received on ends 44, 45 of shaft 43. Lower apertures 62, 63 of front links 56, 57 communicate with the joint chassis 72, shown in FIG. 3F. Also shown is rear link 30 which is mounted between rear wings of housings 11, 12 and supported on pivot pin 32, which is received through apertures 23, 24 of the rear wings and upper aperture 31 of rear link. Washers 33 facilitate rotation of link 30 with respect to the housing wings, and needle bearings 34 facilitate rotation of pivot pin 32.

Paddle assembly 40 comprises paddle 41 which may have an opening 42 to receive rotatable shaft 43 or may be integrally formed with the shaft. Assembly 40 also includes plugs 46, 47, back valves such as check balls 48, 49, O-ring seals 50, and left and right flow control valves such as chokes 51, 52. With reference to FIG. 2A, it may be seen that chokes 51, 52 are received within the ends of the rotatable shaft 43 and that paddle portion 41 has a front side 64 and rear side 65. The paddle portion 41 preferably rotates through an arc centered on the axis of rotatable shaft 43 and generally opposite the upper portions of housings 11, 12. In this fashion, the hydraulic chamber 85 is located substantially below the rotatable shaft 43 which defines the axis of rotation for the paddle portion 41, and chamber 85 adds no additional height to the upper portion of the housings. This permits the upper joining section to be located only a short distance from the center of rotation of rotatable shaft 43. In a prosthetic joint for use by a lower limb amputee having a body weight of 100 kg/220 pounds, the distance from the top of the joining section to the center of rotatable shaft 43 would be only about 2.2 to 2.5 centimeters.

With reference to FIG. 2B, front side 64 is shown with aperture 67 into which hydraulic fluid on the forward side may enter into the paddle 41, and aperture 66 which permits hydraulic fluid from the rear side of paddle 41 to exit into the forward side of chamber 85. It will be understood that the opposite side 65 of paddle 41 has similar apertures to permit the flow of hydraulic fluid in the opposite directions.

FIG. 2C better illustrates how hydraulic fluid may flow through paddle 41. Specifically, when paddle 41 is moving forward through hydraulic chamber 85 toward the forward end of the chamber, as might be the case when the polycentric knee is moving from a state of 45° rear flexion toward full extension, the hydraulic fluid in the forward portion of chamber 85 may enter aperture 67 of forward surface 64 of paddle 41 and proceed through channel 68 and out an opening on the reverse side of paddle 41. Adjusting left flow control valve 51 correspondingly adjusts the rate at which hydraulic fluid may flow through channel 68 and therefore may be utilized to make the polycentric joint more readily extendable when moving in this direction by allowing increased flow, or correspondingly reducing the extendability of the joint toward extension by decreasing the flow. A back valve such as check ball 48 prevents hydraulic fluid from flowing through channel 68 when paddle 41 is moved in the opposite direction toward the rear of hydraulic chamber 85. Indeed, when paddle 41 is moving rearward in chamber 85 toward the rearward end of the chamber, hydraulic fluid enters opening 78 on the rear paddle side and proceeds through channel 69 and exits through opening 66 on the front side 64 of paddle 41. Right flow control valve 52 may be utilized to adjust the rate of flow of hydraulic fluid through channel 69 and thus control the resistance of the polycentric knee toward substantial flexion.

Generally, by properly selecting the hydraulic fluid to match the amputee's activity level, no seals will be required about paddle 41 or the chamber walls by which the paddle passes. Such seals would be subject to heat buildup, and wear or failure. Seals can be utilized if desired, as for instance with a very active user, however, the use of seals will entail additional service to the prosthesis. By utilizing control of fluid flow to adjust the knee's characteristics, the present design eliminates the play and metallic noises inherent in rack and gear designs for hydraulic damping.

FIG. 3A provides a side view of rotary hydraulic chamber assembly 10 secured by front link 56 and rear link 30 to chassis 72. Protruding below chassis 72 is spring cup 95 and spring 96 which are used to provide extension assist to the prosthetic knee as described below. Chassis 72 is designed to mount on a lower prosthetic leg assembly (not shown). FIG. 3E is a perspective view of the prosthetic knee of FIG. 3A in which the top surfaces 13, 14 and grooves 15, 16 can be more clearly seen as forming a dovetail joint in immediate proximity to the rotary hydraulic chamber contained within hydraulic chamber assembly 10. In addition, channel 39 which is provided to facilitate cooling and bumper placement is shown on housing 11. FIG. 3B is a front view of the same prosthetic knee with a partial sectional view to show lever 92. FIG. 3C is a sectional view taken along line A—A of FIG. 3B and shows how lever 92 communicates between rear link 30 and barrel 74. FIG. 3D is taken along line B—B of FIG. 3C and shows a cross section of paddle assembly and bumper 80.

FIGS. 3B and 3E show the dovetail joint formed by top surfaces 13, 14 and grooves 15, 16. In conjunction with channel 94, the dovetail joint allows an upper leg prosthesis to be mounted directly upon the prosthetic knee. Adjusting screws on the upper leg prosthesis may be used in co-operation with channel 94 to slide the upper leg prosthesis along the dovetail joint, and secure the socket in fixed relation to the prosthetic knee. The upper leg prosthesis is secured in a more forward position for greater stability, and a more rearward position for more responsive flexion action in the knee. This dovetail joint may obviate the need for a separate adapter to join the prosthetic knee to the upper leg prosthesis in an adjustable fashion.

FIG. 3F is an exploded view of the entire prosthetic knee assembly and in particular shows bumpers 80 which are mounted in channels of housings 11, 12 and restrained by covers 81, 82 which are held in place by screws 89. Bumpers 80 may be made of different durometer materials to provide different levels of resistance to forward flexion. Bumper covers 81, 82 act as hard stops to forward flexion beyond about 10° to 20° of rotation. FIG. 3F also shows bladder 71 and bladder plugs 70 which are secured within hydraulic chamber 85 in order to provide slight compressibility of the gas within bladder 71. By placing a bladder 71 on either side of paddle 41, a slight compression can be achieved in either direction of paddle movement even without flow of the hydraulic fluid.

Lever assembly comprising lever 92, upper and lower dowels 91, 90, and washers 93, are also illustrated in FIG. 3F. Upper dowel 91 proceeds through slots 88 of lower wings of rear link 30 while lower dowel 90 proceeds through aperture 79 on barrel 74, and lever 92 is held in place between dowels 91 and 92. Barrel 74 also has catch 87 to receive proximal end of a tensile member such as cable 98 which is secured at its opposite distal end to locknut 99, and intermediately the tensile member or cable body extends through spring ferule 97, spring 96, and spring cup 95 into chassis 72. Rotation of rear link 30 about its pivot point on rear axle 76 causes upper dowel 91 to move and communicate movement through lever 92 to barrel 74. As barrel 74 moves counter-clockwise, cable 98 is pulled into the chassis and spring 96 is compressed. Barrel 74 is received within aperture 86 in chassis 72 and secured in place by barrel bearings 73 and fasteners such as button head screws 83. A fastener such as bolt 84 attaches the chassis 72 to a lower prosthetic limb.

Figure 5B:
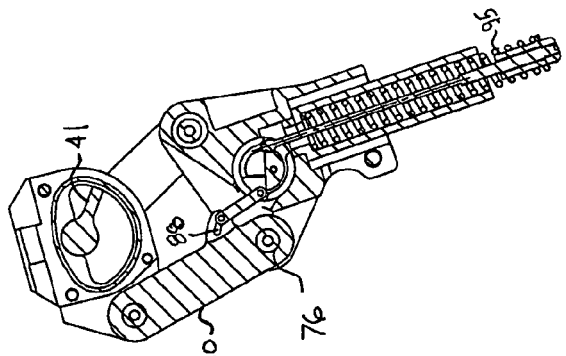
FIG. 5B is a side sectional view of the polycentric knee of FIG. 5A at 15° stance flexion.
Figure 4B:
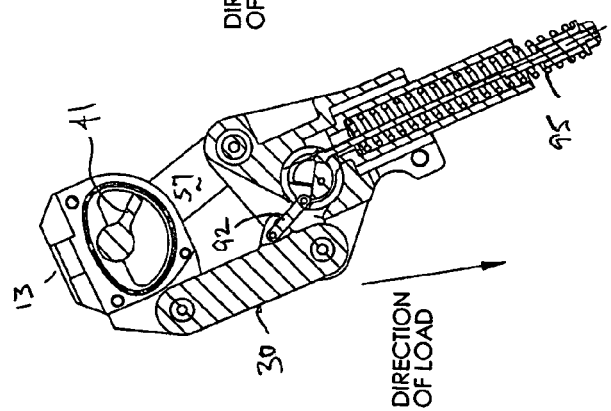
FIG. 4B is a side sectional view of a prosthetic knee according to the invention at full extension.

FIGS. 4A, 5A, 6A, and 7A and corresponding sectional views 4B, 5B, 6B, and 7B show the typical movements of prosthetic knee during the stance phase from initial heel strike to heel lift. In FIG. 4A, the prosthetic knee is at full extension in typical position for heel strike. FIG. 5A represents the prosthetic knee as some load is placed on the prosthetic knee and it can be seen that rear link 30 has rotated about lower rear axle 76 slightly counter-clockwise with respect to chassis 72 exposing slot 88. In addition, front link 56 has rotated counter-clockwise slightly about shaft 43 until, as shown in FIG. 5C, pin 60 has made increasingly resistive contact with bumper 80 until the position of bumper cover 81 has halted counter-clockwise movement after about 15° of rotation or forward flexion. Pin 60 is able to move in an arcuate fashion around the axis of shaft 43 in channel 39. Channel 39 not only permits the motion of pin 60, but also thins the sidewalls of housings 11, 12 and provides additional surface area for heat within the hydraulic chamber to dissipate.

Figure 7B:
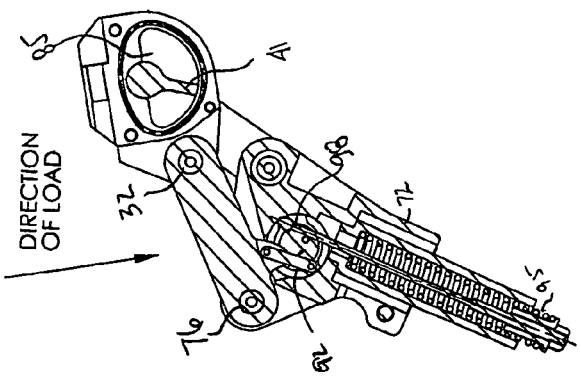
FIG. 7B is a side sectional view of the polycentric knee of FIG. 7A at 45° flexion.
Figure 6B:
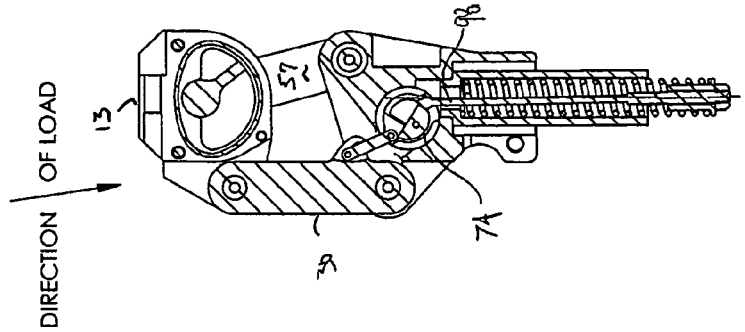
FIG. 6B is a side sectional view of the polycentric knee of FIG. 6A at full extension in mid-stance.

As the step progresses to mid-stance as shown in FIG. 6A, the prosthetic knee is again at full extension. Then, in FIG. 7A, the limb is lagging behind the body and the prosthetic knee is at approximately 45° rear flexion, and it can be seen that rear link 30 has moved clockwise about rear axle 76 and front link 56 has also moved clockwise about shaft 43. Clockwise rotation of link 30 on both rear axles 32, 76 has, as shown in FIG. 7B, caused the downward movement of lever 92 with respect to chassis 72 resulting in the counter-clockwise rotation of barrel 74 thereby pulling cable 98 into chassis 72 and compressing spring 95. The tension in spring 95 will tend to pull the knee back from its rearwardly flexed position into full extension when weight is removed from the limb. Adjustment of both the tension of spring 95 and the flow of hydraulic fluid in chamber 85 from the front of paddle 41 to the rear through channel 68 using flow control valve 51 will vary the speed and force with which the prosthetic knee returns to full extension.

Although preferred embodiments of the present invention have been disclosed in detail herein, it will be understood that various substitutions and modifications may be made to the disclosed embodiment described herein without departing from the scope and spirit of the present invention as recited in the appended claims.

What is claimed is:

1. A polycentric prosthetic knee joint for use in connecting an upper leg prosthesis to a lower prosthetic leg comprising:
   a housing with an upper joining section for connection with the upper leg prosthesis, and a lower section having an arcuate channel therein with a bumper at the forward portion of said channel;
   a forward link having a first end pivotable about a first center of rotation on the lower section of the housing, a pin protruding from the forward link into the arcuate channel, and a second end pivotable about a second center of rotation on a chassis connected to the lower prosthetic leg;
   a rear link having a front end pivotable about a third center of rotation located on the housing rearward of the first center of rotation, and a second end pivotable about a fourth center of rotation located on the chassis rearward of the second center of rotation;
   wherein the bumper in the channel resists the pin on the forward link against forward movement for up to between 10° and 20° of forward flexion by the prosthetic knee joint.

2. The prosthetic knee joint of claim 1 wherein the bumper is secured in place by a bumper cover mounted over a forward portion of the bumper in the channel, and the bumper cover serves as a hard stop against the pin on the forward link beyond said between 10° to 20° of forward flexion.

3. The prosthetic knee joint of claim 1 wherein the lower portion of the housing defines a rotary chamber with forward and rearward ends and containing hydraulic fluid.

4. The prosthetic knee joint of claim 3 wherein the first end of the forward link is connected to a rotatable shaft mounted in an upper portion of the rotary chamber for rotation therewith.

5. The prosthetic knee joint of claim 4 wherein a paddle generally interfitting with the rotary chamber is mounted to the rotatable shaft and is adapted for reciprocable rotary movement with the rotatable shaft within the rotary chamber wherein the axis of rotation of the rotatable shaft is in the upper portion of the rotary chamber and rotary movement of the paddle is substantially in a lower portion of the rotary chamber.

6. The polycentric prosthetic knee joint of claim 3 wherein:
 a rotatable paddle assembly having a rotatable shaft is mounted intermediate the forward and rearward ends of the chamber, said paddle interfitting within the chamber and being adapted for reciprocable rotary movement between the forward end and the rearward end of the chamber;
 a first channel within the rotatable paddle assembly permits unidirectional flow of hydraulic fluid only from the forward end of the chamber to the rearward end of the chamber; and
 a second channel within the rotatable paddle assembly permits unidirectional flow of hydraulic fluid only from the rearward end of the chamber to the forward end of the chamber.

7. The rotary hydraulic chamber assembly of claim 6 wherein a back valve in the first channel prevents the flow of hydraulic fluid from the rearward end of the chamber to the forward end of the chamber.

8. The rotary hydraulic chamber assembly of claim 6 wherein an adjustable flow control valve controls the rate at which hydraulic fluid may flow through the first channel from the forward end of the chamber to the rearward end of the chamber.

9. A polycentric prosthetic knee joint for use in connecting an upper leg prosthesis to a lower prosthetic leg comprising:
 a housing with an upper joining section for connection with the upper leg prosthesis and a lower section, wherein the lower section of the housing defines a rotary chamber with forward and rearward ends therein and containing hydraulic fluid, and further comprises a rotatable paddle assembly having a rotatable shaft mounted intermediate the forward and rearward ends of the chamber, said shaft having a paddle extending therefrom, the paddle interfitting within the chamber and being adapted for reciprocable rotary movement between the forward and rearward ends of the chamber;
 a forward link having a first end pivotable about a first center of rotation on the lower section of the housing and a second end pivotable about a second center of rotation on a chassis connected to the lower prosthetic leg;
 a rear link having a first end pivotable about a third center of rotation located on the housing rearward of the first center of rotation, and a second end pivotable about a fourth center of rotation located on the chassis rearward of the second center of rotation;
 a lever having a first end in communication with the rear link and a second end in communication with a barrel mounted for rotation within the chassis;
 an extension assist mechanism having a tensile member with a first tensile member end connected to the rotatable barrel, a tensile member body passing through a spring with a proximal end fixedly received in the chassis, and a second tensile member end connected a distal end of the spring extending away from the joint;
 wherein motion of the rear link relative to the fourth center of rotation causes the barrel to rotate and retract a portion of the tensile member toward the joint thereby compressing the spring.

10. The polycentric prosthetic knee assembly of claim 9 wherein the rotatable paddle assembly further comprises:
 a first channel within the rotatable paddle assembly permitting uni-directional flow of hydraulic fluid only from the forward end of the chamber to the rearward end of the chamber; and
 a second channel within the rotatable paddle assembly permitting uni-directional flow of hydraulic fluid only from the rearward end of the chamber to the forward end of the chamber.

11. A polycentric prosthetic knee joint for use in connecting an upper leg prosthesis to a lower prosthetic leg comprising:
 a housing with an upper joining section for connection with the upper leg prosthesis, and a lower section having an arcuate channel therein with a bumper at the forward portion of said channel;
 a forward link having a first end pivotable about a first center of rotation on the lower section of the housing, a pin protruding from the forward link into the arcuate channel, and a second end pivotable about a second center of rotation on a chassis connected to the lower prosthetic leg;
 a rear link having a front end pivotable about a third center of rotation located on the housing rearward of the first center of rotation, and a second end pivotable about a fourth center of rotation located on the chassis rearward of the second center of rotation said bumper at the forward portion of the channel resisting the pin on the forward link against about 15° of forward flexion by the prosthetic knee joint;
 a lever having a first end in communication with the rear link and a second end in communication with a barrel mounted for rotation within the chassis;
 an extension assist mechanism having a cable with a first cable end connected to the rotatable barrel, a cable body passing through a spring with a proximal spring end fixedly received in the chassis, and a second cable end connected to a distal spring end extending away from the joint, such that motion of the rear link relative to the fourth center of rotation causes the barrel to rotate and retract a portion of the cable toward the joint thereby compressing the spring;
 the lower section of the housing defining a rotary chamber with forward and rearward ends therein and containing hydraulic fluid;
 a rotatable paddle assembly having a rotatable shaft mounted intermediate the forward and rearward ends of the chamber, and a paddle mounted to the rotatable shaft, generally interfitting with the rotary chamber, and adapted for reciprocable rotary movement about the rotatable shaft within the rotary chamber;
 a first channel within the rotatable paddle assembly permitting uni-directional flow of hydraulic fluid only from the forward end of the chamber to the rearward end of the chamber; and
 a second channel within the rotatable paddle assembly permitting uni-directional flow of hydraulic fluid only from the rearward end of the chamber to the forward end of the chamber;
 wherein the rotatable shaft is mounted in an upper portion of the rotary chamber and the arc of rotation of the paddle is generally opposite the rotatable shaft from the upper joining section.

* * * * *